US012018305B2

United States Patent
Syed et al.

(10) Patent No.: US 12,018,305 B2
(45) Date of Patent: Jun. 25, 2024

(54) **PROCESS FOR PRODUCTION OF NIGERICIN FROM *STREPTOMYCES* SP. MCC-0151**

(71) Applicant: Council of Scientific & Industrial Research, New Delhi (IN)

(72) Inventors: Gulam Dastager Syed, Pune (IN); Amit Kumar Sahu, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 357 days.

(21) Appl. No.: 17/311,783

(22) PCT Filed: Dec. 10, 2019

(86) PCT No.: PCT/IN2019/050900
§ 371 (c)(1),
(2) Date: Jun. 8, 2021

(87) PCT Pub. No.: WO2020/121324
PCT Pub. Date: Jun. 18, 2020

(65) Prior Publication Data
US 2022/0025418 A1    Jan. 27, 2022

(30) Foreign Application Priority Data
Dec. 10, 2018   (IN) .............................. 201811046548

(51) Int. Cl.
*C12P 17/18*   (2006.01)
*C12N 1/20*    (2006.01)
*C12R 1/465*   (2006.01)

(52) U.S. Cl.
CPC ............ *C12P 17/181* (2013.01); *C12N 1/205* (2021.05); *C12R 2001/465* (2021.05)

(58) Field of Classification Search
CPC .. C12P 17/181; C12N 1/205; C12R 2001/465
See application file for complete search history.

(56) References Cited

FOREIGN PATENT DOCUMENTS

| CN | 102174051 A | * | 9/2011 |
|---|---|---|---|
| CN | 102174051 A | | 9/2011 |
| CN | 103540547 A | | 1/2014 |
| CN | 103642723 A | | 3/2014 |

OTHER PUBLICATIONS

Gumila et al., "Characterization of the Potent In Vitro and In Vivo Antimalarial Activities of Ionophore Compounds", Antimicrobial Agens and Chemotherapy, vol. 41, No. 3, pp. 523-529, Mar. 1997.

(Continued)

*Primary Examiner* — Gary B Nickol
*Assistant Examiner* — Amelia Nicole Dickens
(74) *Attorney, Agent, or Firm* — Dinsmore & Shohl LLP

(57) ABSTRACT

A fermentation process is provided for the synthesis of Nigericin from *Streptomyces* sp. having accession number MCC 0151 and its isolation with high yield. A microbial inoculant composition is provided, comprising a biologically pure culture of *Streptomyces* sp. MCC 0151 for the exclusive production of Nigericin with high yield.

9 Claims, 7 Drawing Sheets

(56) References Cited

OTHER PUBLICATIONS

Mouslim et al., "Biosynthetic Study on the Polyether Carboxylic Antibiotic, Nigericin Production and Biohydroxylation of Grisorixin by Nigericin-producing Streptomyces hygroscopicus NRRL B-1865", The Journal of Antibiotics, vol. 48, No. 9, pp. 1011-1014, Sep. 1995.

Taechowisan et al., "Antibacterial activity of 1-methyl ester-nigericin from Streptomyces hygroscopicus BRM10; an endophyte in Alpinia galanga", Journal of Applied Pharmaceutical Science, vol. 3, No. 5, pp. 104-109, May 2013.

International Search Report and Written Opinion pertaining to PCT/IN2019/050900 dated Jun. 4, 2020.

\* cited by examiner

PROCESS FOR PRODUCTION OF NIGERICIN FROM *STREPTOMYCES* SP. MCC-0151

CROSS-REFERENCES TO RELATED APPLICATIONS

This application is a national-stage application under 35 U.S.C. § 371 of International Application No. PCT/IN2019/050900, filed Dec. 10, 2019, which International Application claims benefit of priority to Indian Application No. 201811046548, filed Dec. 10, 2018.

TECHNICAL FIELD

The present disclosure relates to a fermentation process for synthesis of nigericin from *Streptomyces* sp. having accession number MCC 0151 with high yield. The present disclosure further relates to a microbial composition comprising a biologically pure culture of *Streptomyces* sp. MCC 0151 as an inoculant for the production of nigericin.

BACKGROUND

The nigericin antibiotic produced by *Streptomyces*, notably *Streptomyces hygroscopicus* was first isolated in the 1950s. Its complex structure was finally elucidated in 1968. Nigericin is an ionophore, possessing very high affinity for monovalent cations such as $Na^+$ and $K^+$. Nigericin disrupts membrane potential of mitochondria. Although nigericin can be isolated as a free acid, like most ionophores, it is extracted into organic solvents and is most conveniently isolated as a salt. Through in-vitro techniques, it has been established that nigericin has broad biological activity against Gram-positive bacteria, fungi, tumor cell lines, malarial parasites and certain viruses, including HIV.

A total of 53 bacteria of the Streptomycetaceae family have been reported to produce ionophores. These microorganisms belong to three genera, *Streptomyces, Actinomadura* and *Dactylosporangium*. *Streptomyces* are considered to be the main producers of ionophores. Approximately, 50% of the ionophores known at present are derived from two *Streptomyces* species (i.e., *Streptomyces hygroscopicus* and *Streptomyces albus*). Nigericin was among the first polyether ionophores to be discovered, but its biosynthesis still remains obscure, therefore, casting a strain on its production, yield and commercialization.

Structurally, nigericin displays cyclic ether with branched-chain having a terminal carboxylic group, and are characterized by the presence of many stereogenic centres. The molecular formula of nigericin is $C_{40}H_{68}O_{11}$, with a molar mass of 724.96 g/mol.

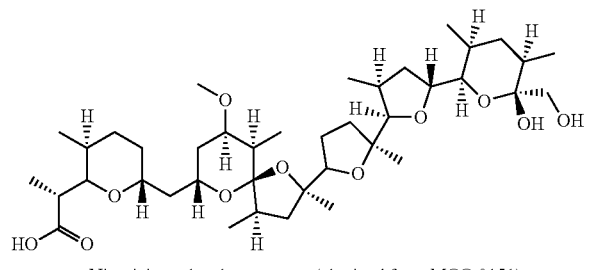

Nigericin molecular structure (obtained from MCC-0151)

Nigericin contains nineteen defined atom stereocenters on the backbone of 40 carbon atoms with 9 rotatable bonds. It has 3 hydrogen bond donor groups associated with 11 hydrogen bond acceptor count. It has been well-established by analytical parameters such as NMR, XRD, IR etc. Nigericin is commercially available from very few global fermentation industries.

A research study relating to biosynthetic study on the polyether carboxylic antibiotic, nigericin production and biohydroxylation of grisorixin by nigericin-producing *Streptomyces hygroscopicus* NRRL B-1865 published in *The Journal of Antibiotics*, Vol, 4, No. 9, 1995 by Mouslim et al, discloses that the addition of methyl oleate, increases the yield of nigericin production and also resulted in the isolation of three additional polyether antibiotics-abierixin, epinigericin, and grisorixin. However, the yield of nigericin was observed to be as less as 8 mg/L in said disclosure. Further, the production of both abierixin and grisorixin by nigericin producing *S. hygroscopicus* NRRLB-1 865 poses the problem of final steps of biosynthesis of the major metabolite nigericin. In a different study on "strain for producing nigericin" has been reported with Chinese patent application number 20111067581 dated Mar. 21, 2011, wherein authors have described *Streptomyces malaysiensis* 04-6 which produces nigericin and its application in alga killing. However, in this report, they have not detailed the process on the subject of recovery, yield and economy of the process.

Presently, nigericin is produced by *Streptomyces hygroscopicus* and is available through commercial suppliers only for research purposes at an exorbitant cost due to its significant low production yield. Commercially, nigericin is obtained as a byproduct, or as a contaminant, during a process of fermentation of geldanamycin, therefore, a process for exclusive production of nigericin has not been reported in the prior art. It is concluded from above that the prior art disclosures lack a defined process for the production and isolation of nigericin having efficient antibiotic attributes.

Therefore, there is a need in the art to provide a cost-efficient process for exclusive production of nigericin giving high yield.

An object of the present disclosure is to provide a fermentation process for synthesis of nigericin, wherein nigericin is produced as the main product with high yield.

Another object of the present disclosure is to provide a process for isolation of nigericin from a whole-cell broth extract.

Yet another object of the present disclosure is to provide a composition comprising *Streptomyces* sp. having accession number MCC 0151 for exclusive synthesis of nigericin.

SUMMARY

An embodiment, as described herein, provides a process for synthesis of nigericin from *Streptomyces* sp. MCC 0151 comprising:
  (i) culturing an inoculum comprising *Streptomyces* sp. MCC 0151 in a metabolite production medium;
  (ii) mixing the metabolite production medium containing the *Streptomyces* sp. MCC 0151 cells and ethyl acetate in a ratio of 1:1 to obtain a mixture;
  (iii) centrifuging the mixture obtained in step (ii) to obtain a supernant and an ethyl acetate extract comprising nigericin;
  (iv) evaporating the ethyl acetate extract obtained in step (iii) to obtain a dried crude extract;

(v) purifying the dried crude extract obtained in step (iv) by column chromatography to obtain a purified nigericin, wherein nigericin is produced having a high yield with concentration up to 500 mg/L.

Yet another embodiment, as described herein, provides, wherein the inoculum comprises *Streptomyces* sp. MCC 0151 in a concentration ranging from 5% to 10% by volume of the metabolite production medium.

In still another embodiment, as described herein, the culturing is carried out at a temperature range of 28° C. to 32° C. for 5-8 days.

In yet another embodiment, as described herein, the column chromatography comprises a silica gel mesh as a stationary phase and a gradient comprising dichloromethane and methanol as a mobile phase.

In still another embodiment, as described herein, the metabolite production medium comprises a carbon source, yeast extract as a nitrogen source, $K_2HPO_4$, and $MgSO_4 \cdot 7H_2O$.

In still another embodiment, as described herein, the carbon source is selected from the group consisting of starch.

In still another embodiment, as described herein, the nigericin produced has a yield of 33% by weight.

In still another embodiment, as described herein, the nigericin produced has an anti-bacterial and anti-malarial property.

Still another embodiment, as described herein, provides a microbial composition comprising a biologically pure culture of *Streptomyces* sp. having accession number MCC-0151 in a concentration ranging from 5% to 10% by weight of the metabolite production medium and a suitable excipient.

Still another embodiment, as described herein, provides a process for synthesis of nigericin from *Streptomyces* sp. MCC 0151, wherein nigericin is produced as a major metabolite having a high yield with concentration up to 500 mg/L.

BRIEF DESCRIPTION OF DRAWINGS

FIG. 9A depicts the NOSY NMR spectra, FIG. 9B depicts the HSQC NMR spectra, FIG. 9C depicts the HMBC NMR spectra and FIG. 9D depicts the COSY NMR spectra.

DETAILED DESCRIPTION

Various embodiments will now be described in detail in connection with certain preferred and optional embodiments, so that various aspects thereof may be more fully understood and appreciated.

Source of Biological Material:

*Streptomyces* sp. DASNCL-29 producing nigericin was isolated from soil which was collected from Unkeshwar, Maharashtra, India (GPS: 20° 05'57.8" N 78° 20' 17.4"E).

Deposit of Biological Material

In accordance with the present disclosure, the strain of *Streptomyces* sp. DASNCL-29 has been deposited at the National Center for Microbial Resource, Pune, Maharashtra, India on 7 Sep. 2018 and has been assigned the accession number: MCC 0151.

Figure 6:
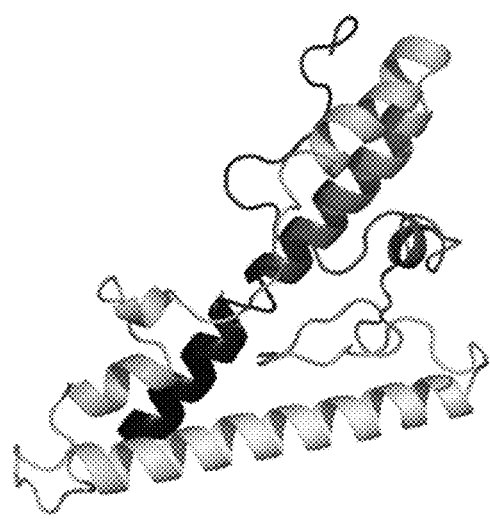
FIG. 6 depicts the additional transport-related protein in *Streptomyces* sp. MCC 0151.

*Streptomyces* sp. MCC 0151 of the present disclosure has natural nigericin biosynthetic gene cluster associated in its genome like other nigericin producing strains. Along with natural nigericin biosynthetic gene cluster, this strain has an additional transport-related gene. The protein of the same is provided in FIG. 6. Said gene has not been reported to be associated with any known nigericin producing strains. This transporter protein transports the large molecule extra cellularly, which leads the high yield of nigericin in the present disclosure. Therefore, to enhance nigericin production from *Streptomyces* MCC 0151 and to obtain nigericin in high yield, the present disclosure provides a process which is specific to *Streptomyces* MCC 0151.

The present disclosure provides a process for production and isolation of nigericin from *Streptomyces* sp. MCC 0151. This process involves the use of the novel strain *Streptomyces* sp. MCC 0151. The process is strain specific as all strains do not produce nigericin with routine process.

The present disclosure provides a process for production and isolation of nigericin from *Streptomyces* sp. MCC 0151 comprising culturing *Streptomyces* sp. MCC 0151 in a metabolite production medium and after culture for suitable days, subjecting the medium containing *Streptomyces* sp. MCC 0151 to solvent extraction using ethyl acetate. The ethyl acetate extract comprising nigericin is subjected to evaporation to obtain a dried crude extract and purifying the dried crude extract by column chromatography to obtain a fraction containing purified nigericin. The Nigericin produced by process of the present disclosure is the main product in high yield, unlike conventional processes which involve producing nigericin as a contaminant or as a byproduct. The complete workflow of the claimed process is very specific to the *Streptomyces* sp. MCC 0151 for high yield of nigericin. Nigericin produced by the process of the present disclosure has been proved to be effective as an antimicrobial and anti-malarial agent. Keeping the commercial aspect of the production of nigericin, it is very important to have an economical process for production of nigericin.

The present disclosure provides a process for synthesis of nigericin from *Streptomyces* sp. MCC 0151, wherein nigericin is produced as a major metabolite having a high yield with concentration up to 500 mg/L.

An embodiment, as described herein, provides a process for synthesis of nigericin from *Streptomyces* sp. MCC 0151 comprising:
(i) culturing an inoculum comprising *Streptomyces* sp. MCC 0151 in a metabolite production medium;
(ii) mixing the metabolite production medium containing the *Streptomyces* sp. MCC 0151 cells and ethyl acetate in a ratio of 1:1 to obtain a mixture;
(iii) centrifuging the mixture obtained in step (ii) to obtain a supernant and an ethyl acetate extract comprising nigericin;
(iv) evaporating the ethyl acetate extract obtained in step (iii) to obtain a dried crude extract;
(v) purifying the dried crude extract obtained in step (iv) by column chromatography to obtain a purified nigericin.

Prior to the process for synthesis of nigericin, an inoculum of said *Streptomyces* sp. MCC 0151 strain is prepared by culturing said strain in an International *Streptomyces* Project Medium-2 (ISP 2) agar medium and then transferring it into a liquid cultivation media (LCM) to provide an inoculum comprising *Streptomyces* sp. MCC-0151. The said LCM is incubated in a shaking incubator at 28° C., 150 rpm for 6 days. The liquid cultivation medium comprises soya meal as a nitrogen source, and glucose and mannitol as carbon sources.

Another embodiment, as described herein, provides a liquid cultivation medium for preparing inoculum of *Streptomyces* sp. MCC-0151 comprising 20.0 g/L soya meal, 20.0 g/L mannitol, 4.0 g/L glucose, at pH 7.0±0.3.

In yet another embodiment, as described herein, there is provided a process for synthesis of nigericin from *Streptomyces* sp. MCC 0151, wherein the inoculum comprises *Streptomyces* sp. MCC 0151 in a concentration ranging from 5% to 10% by volume of the metabolite production medium.

In still another embodiment, as described herein, there is provided a process for synthesis of nigericin from *Streptomyces* sp. MCC 0151, wherein the culturing is carried out at a temperature range of 28° C. to 32° C. for 5-8 days.

In another embodiment, as described herein, there is provided a process for synthesis of nigericin from *Streptomyces* sp. MCC 0151, wherein the column chromatography comprises a silica gel mesh as a stationary phase and a gradient comprising dichloromethane and methanol as a mobile phase.

In yet another embodiment, as described herein, there is provided a process for synthesis of nigericin from *Streptomyces* sp. MCC 0151, wherein the metabolite production medium comprises a carbon source, yeast extract as a nitrogen source, $K_2HPO_4$, and $MgSO_4 \cdot 7H_2O$.

In still another embodiment, as described herein, there is provided a process for synthesis of nigericin from *Streptomyces* sp. MCC 0151, wherein the carbon source in metabolite production medium is selected from the group consisting of glucose and mannitol.

In another embodiment, as described herein, there is provided a process for synthesis of nigericin from *Streptomyces* sp. MCC 0151, wherein the nigericin produced has a yield of 33% by weight.

In yet another embodiment, as described herein, there is provided a process for synthesis of nigericin from *Streptomyces* sp. MCC 0151, wherein the nigericin produced has an anti-bacterial and anti-malarial property.

Another aspect, as described herein, provides a microbial composition comprising a biologically pure culture of *Streptomyces* sp. having accession number MCC-0151 in a concentration ranging from 5% to 10% by weight of the metabolite production medium and a suitable excipient.

In a preferred embodiment, as described herein, the suitable excipient is a milk medium. *Streptomyces* mycelium with spores can be kept in lyophilized form using milk medium, or in soil base for long duration and can be revived to be used for inoculation.

Yet another aspect, as described herein, provides a microbial composition comprising a biologically pure culture of *Streptomyces* sp. having accession number MCC-0151 in a concentration ranging from 5% to 10% by volume of the metabolite production medium and a metabolite production medium consisting of a carbon source, a nitrogen source and mineral sources.

In yet another aspect, as described herein, there is provided a microbial composition comprising a biologically pure culture of *Streptomyces* sp. having accession number MCC-0151 in a concentration ranging from 5% to 10% by volume of the metabolite production medium and a metabolite production medium, wherein in the metabolite production medium, the carbon source is selected from glucose or mannitol, the nitrogen source is selected from yeast extract or soya extract and the mineral source is selected from $K_2HPO_4$, and $MgSO_4 \cdot 7H_2O$.

Accordingly, the fermentation process for synthesis of nigericin comprises the following stages, which are thereafter described in detail:
(i) Developing an inoculum of *Streptomyces* sp. MCC-0151,
(ii) Upstream processing for metabolite production, and
(iii) Downstream process for extraction and purification of nigericin.

Inoculum Development:

The nigericin producing *Streptomyces* sp. MCC-0151 is inoculated from ISP 2 agar into a liquid cultivation medium (LCM). The LCM comprises Soya meal (20.0 g/L), mannitol (20.0 g/L), glucose (4.0 g/L), at pH 7.0±0.3. LCM is incubated in shaking incubator at 28° C., 150 rpm for 6 days.

Fermentation Process (Upstream):

The metabolite production medium comprises starch (15 g/L), yeast extract (4 g/L), $K_2HPO_4$ (1g/L), $MgSO_4 \cdot 7H_2O$ (0.5 g/L). 10% by weight of the inoculum prepared from LCM is inoculated aseptically into said metabolic production medium.

Temperature: 28° C., Agitation: 150 rpm initially (Controlled loop to maintain DO) (Range 150-500 RPM using Ruston turbine impellers, Aeration: Compressed Sterile Air 3 LPM through macro sparger (Adjusted to maintain DO) Dissolved Oxygen (DO): initially saturated to 100%. maintained to 30±5%. Duration: 6 days, pH: 7.0+0.3

Downstream Process Purification

Ethyl Acetate Extraction

Ethyl acetate is used to extract the metabolite produced from whole fermentation broth (metabolite production medium containing *Streptomyces* sp. MCC 0151 cells). Ethyl acetate and the metabolite production medium containing the *Streptomyces* sp. MCC 0151 cells mixed in a 1:1 ratio are centrifuged and the ethyl acetate extract containing nigericin is subjected to rotary vacuum evaporation to obtain a dried crude extract (75 g/50 L).

Chromatography Purification:

Purification is performed by column chromatography using a gravity column with silica gel mesh 100-200 as stationary phase and gradient of dichloromethane and methanol as a mobile phase.

The Crude extract (75 g) is fractionated into 45 fractions, thereafter, the fraction containing nigericin is mixed together and further purified using the same chromatographic method to obtain 25 g pure nigericin.

In yet another embodiment, as described herein, there is provided a process for synthesis of nigericin from *Streptomyces* sp. MCC 0151, wherein nigericin is exclusively produced as a main product and the yield of nigericin is in a concentration of up to 500 mg/L in pilot-scale production of 10 L to 50 L.

After culture, the microbial production medium comprises nigericin in a concentration ranging from 0.2 µg/mL to 80 µg/mL, preferably, in a concentration ranging from 0.2 µg/mL to 50 µg/mL, more preferably, in a concentration ranging from 20 µg/mL to 50 µg/mL.

The nigericin synthesised by the process described herein has both anti-bacterial and anti-malarial properties. The nigericin has MIC of 0.21 µg/mL against *Staphylococcus aureus* and MIC Conc. of 287.7 nM. The nigericin has $IC_{50}$ ~0.986 nM against *P. falciparum*.

The nigericin synthesized by the process as described herein exhibits excellent bioavailability and is not toxic to the host cells.

An embodiment as described herein provides a composition comprising nigericin for treatment of infectious diseases and malaria.

EXAMPLES

The following examples are given by way of illustration of the present disclosure and therefore should not be construed to limit the scope of the present disclosure.

Example 1

Inoculum Development

For establishing an inoculum for production of nigericin, the *Streptomyces* sp. MCC-0151 was initially grown on ISP2 agar plate to obtain pure colonies. A single colony was picked up from the plate and was inoculated aseptically into a sterile liquid cultivation medium containing soya meal 20 g/L, mannitol 20 g/L, Glucose 4 g/L having pH 7.0±0.3 with 5% to 10% inoculum and was kept under shaking condition at a temperature of 28° C., with 150 RPM for 6 days.

Example 2

Upstream Process i.e. Nigericin Production

Nigericin production was carried out in a pilot scale using 14 L fermenter. Metabolite Production Medium containing Starch 15 g/L, Yeast Extract 4 g/L, di-potassium hydrogen phosphate lg/L and magnesium sulphate heptahydrate 0.5 g/L was inoculated aseptically with the inoculum developed in the liquid cultivation medium.

Example 3

Process Parameters (a) Temperature
The temperature of the process was maintained to 28° C. using a jacketed temperature controlling system.
(b) Dissolved Oxygen
Dissolved oxygen in the fermentation medium was calibrated to 100% by saturating the medium with oxygen at room temperature before inoculating the fermenter. During the process, the dissolved oxygen was maintained to 30±5% using cascade controlled system looped with the agitation.
(c) Agitation:
Proper mixing of the process was obtained using motor-driven Ruston turbine impellers controlled to achieve the desired dissolved oxygen in the process. The rotation was set to a limit of 150 rpm-500 rpm controlled by cascade. The baffled vessel was used to ensure proper mixing.
(d) Aeration:
Sterile air was provided into the medium in the form of sparger air as well as surface air; sparger air 1-5 LPM was used to maintain the dissolved oxygen level in the process. Surface air was provided to keep the vessel under positive pressure to avoid contamination during fermentation run.
(e) Fermentation Volume and Duration:
The fermentation process was carried out in a 14 L vessel with a working volume of 10 L containing 9 L of the metabolite production medium and 1 L of inoculum grown in the liquid cultivation medium. The process was run for 6 days and nigericin production during the process was confirmed by intermittent sampling and observing the bioactivity profile.

Example 4

Downstream Process (a) Ethyl Acetate Extraction
The whole fermentation broth (metabolite production medium containing the *Streptomyces* sp. MCC 0151 cells) was subjected to an extraction using an equal quantity of ethyl acetate in a mixing vessel. Vigorous mixing for 1 hr was carried out to ensure proper extraction of metabolites. After mixing, the mixture of fermentation broth and ethyl acetate was subjected to centrifugation at a speed of 10000 rpm for 10 min and the supernatant was collected. The remaining fermentation broth was again subjected to the extraction twice. The ethyl acetate extract comprising the nigericin was concentrated using a rotary vacuum evaporator to obtain a dried crude extract comprising the nigericin.
(b) Purification of Nigericin
The dried crude extract obtained was fractionated by column chromatography using a gravity column having silica mesh of 100-200 size as a stationary phase. The crude extract was loaded onto the column using 60-120 silica mesh. A fraction containing nigericin was further purified using same chromatographic technique.

Figure 7:
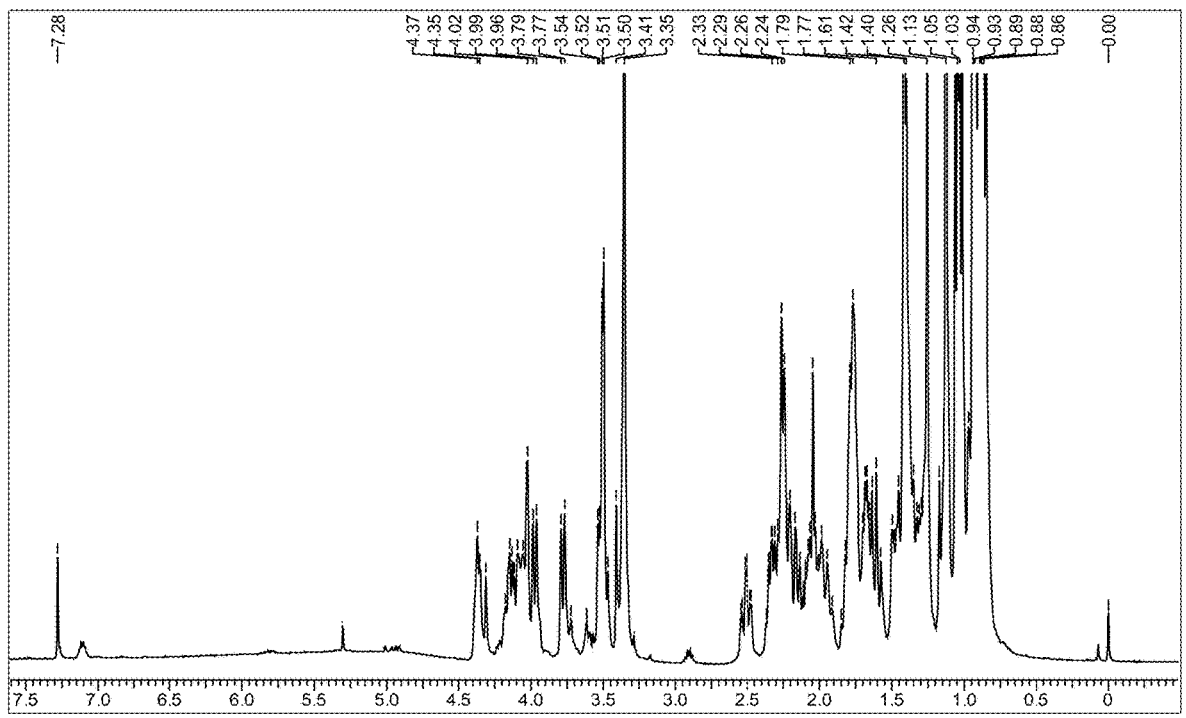
FIG. 7 provides the $^1H$ NMR spectra of obtained nigericin.
Figure 8:
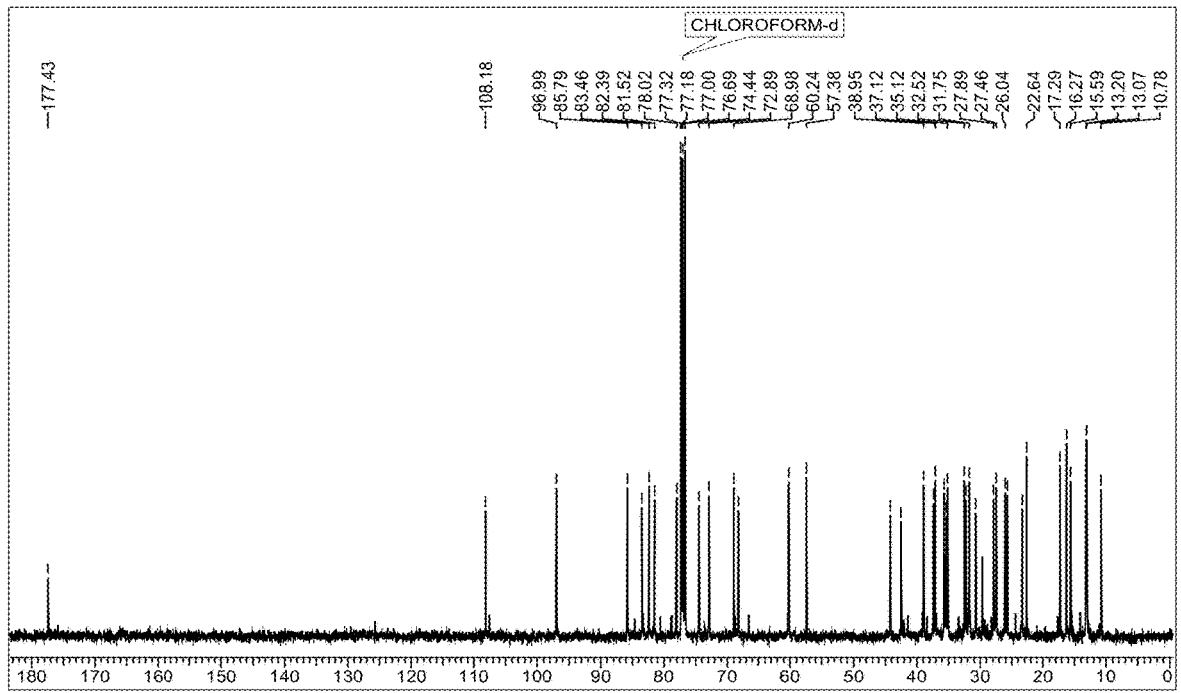
FIG. 8 provides the $^{13}C$ NMR spectra of obtained nigericin.
Figure 9A:
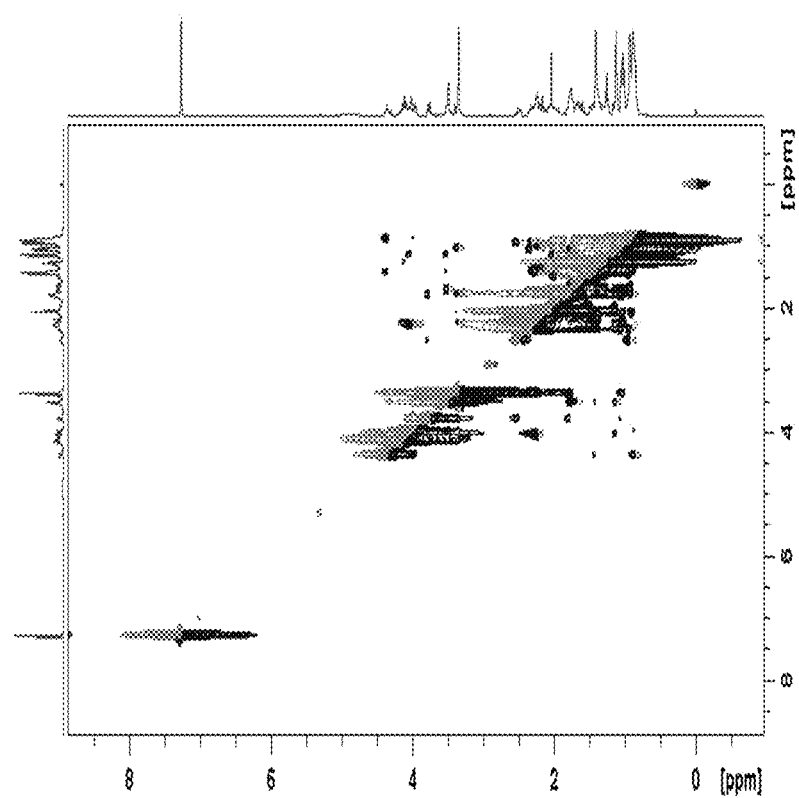
FIG. 9A-9D provide the 2D NMR of obtained nigericin.
Figure 9B:
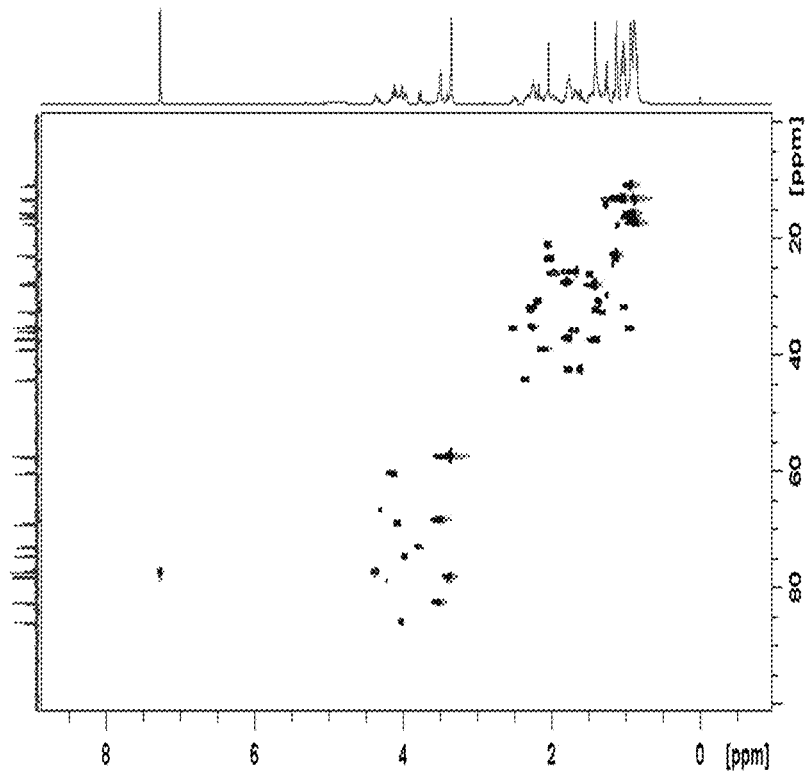
Figure 9C:
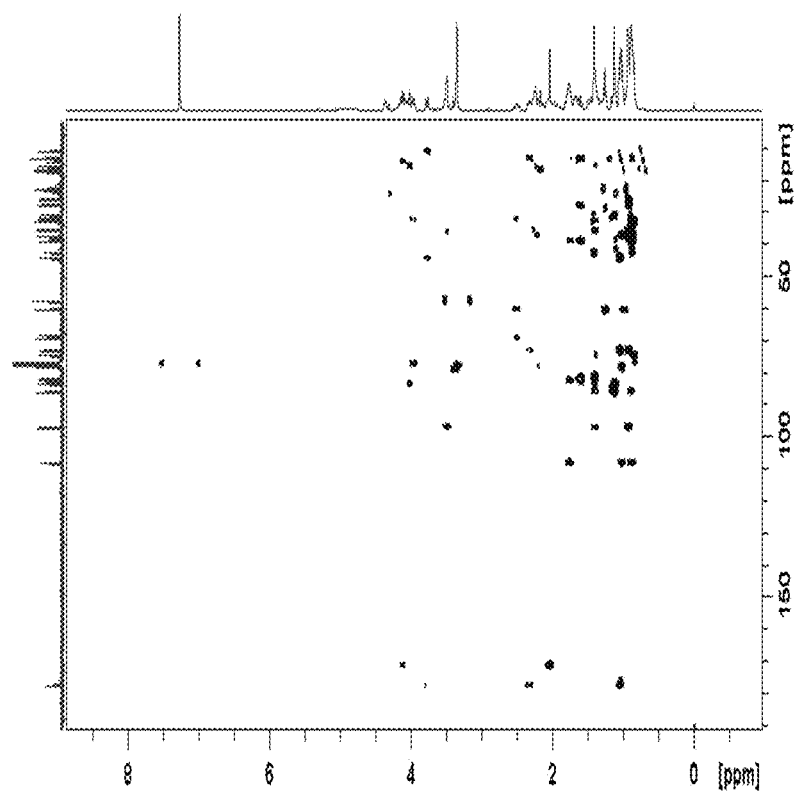
Figure 9D:
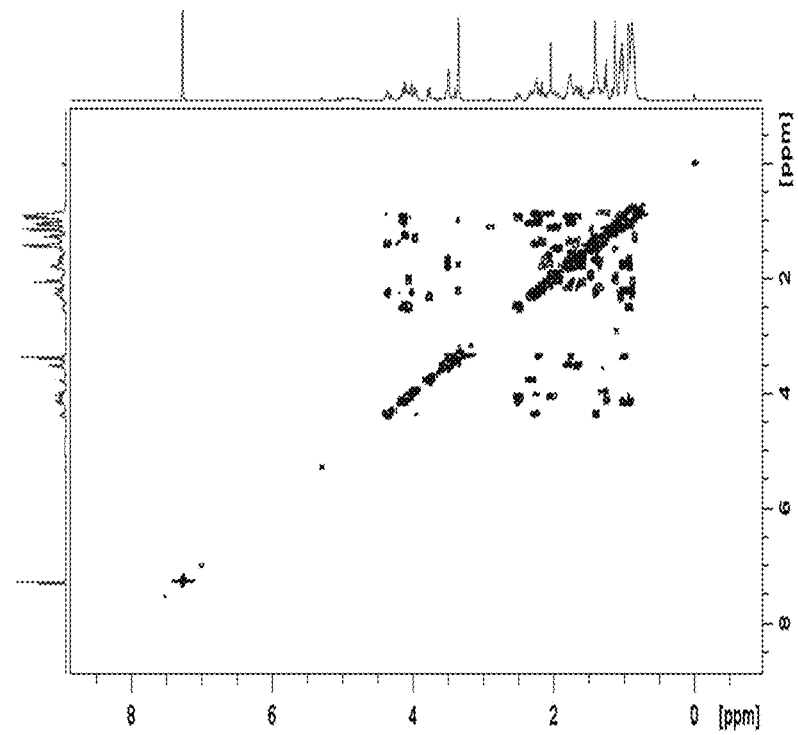

The chromatographic fractionation was carried out using a gradient of dichloromethane and methanol as a mobile phase. The purity of nigericin was analyzed using thin layer chromatography; wherein para anisaldehyde was used as developing reagent for TLC.
(c) Characterization of Nigericin Using NMR Spectroscopy
NMR spectrum for the pure compound was generated using 400 Hz NMR spectrophotometer. Proton NMR, $^{13}C$, HMBC, HSQC, NOSY, COSY spectrum was used to confirm the structure of Nigericin. FIG. 7 provides the $^1H$ NMR spectra of obtained nigericin. FIG. 8 provides the $^{13}C$ NMR spectra of obtained nigericin. FIG. 9 provides the 2D NMR of obtained nigericin. FIG. 9A depicts the NOSY NMR spectra, FIG. 9B depicts the HSQC NMR spectra, FIG. 9C depicts the HMBC NMR spectra and FIG. 9D depicts the COSY NMR spectra.

Example 5

Yield of Nigericin in 50 L Pilot-Scale Fermentation

Pilot-scale fermentation of 50 L volume resulted in 75 g of crude ethyl acetate extract i.e. 1.5 g/L, upon purification 25 g pure nigericin was isolated which accounts for 33% of total crude extract. The calculation of yield is provided in Table 1.

TABLE 1

| Calculation of yield | |
|---|---|
| Fermentation volume | 50 L |
| Crude Extract | 75 g |
| Crude yield | 1.5 g/l |
| Nigericin Isolated | 25 g/50 liters [0.5 g/l, i.e. 500 mg/L] |
| Nigericin (Yield %) | Approx. 33% |

Example 6

Detailed Cost Involved in the Process of Nigericin Production in Pilot Scale (Table 2)

TABLE 2

| | Item | Quantity Used (g/50 L) | Price (INR/Gram) | Total cost (INR) |
|---|---|---|---|---|
| Liquid Cultivation | Soymeal | 100 | 0.47 | 47.00 |
| | D-Mannitol | 100 | 2.80 | 280.00 |
| | Glucose | 20 | 0.69 | 13.80 |
| Production Media | Starch | 750 | 2.60 | 1950.00 |
| | Yeast Extract | 200 | 2.59 | 518.00 |
| | $K_2HPO_4$ | 50 | 2.04 | 102.00 |
| | $MgSO_4 \cdot 7H_2O$ | 25 | 0.58 | 14.50 |
| Downstream Purification | Silica gel | 5000 | 0.78 | 3900.00 |
| | Dichloromethane | 30000 | 0.054 | 1620.00 |
| | Methanol | 10000 | 0.032 | 320.00 |
| | Ethyl acetate | 100000 | 0.06 | 6000 |
| Total production cost per 25 g nigericin from *Streptomyces* sp. MCC-0151 (Excluding Electricity and Manpower). | | ~14765.30 (INR) | | |

Figure 3:
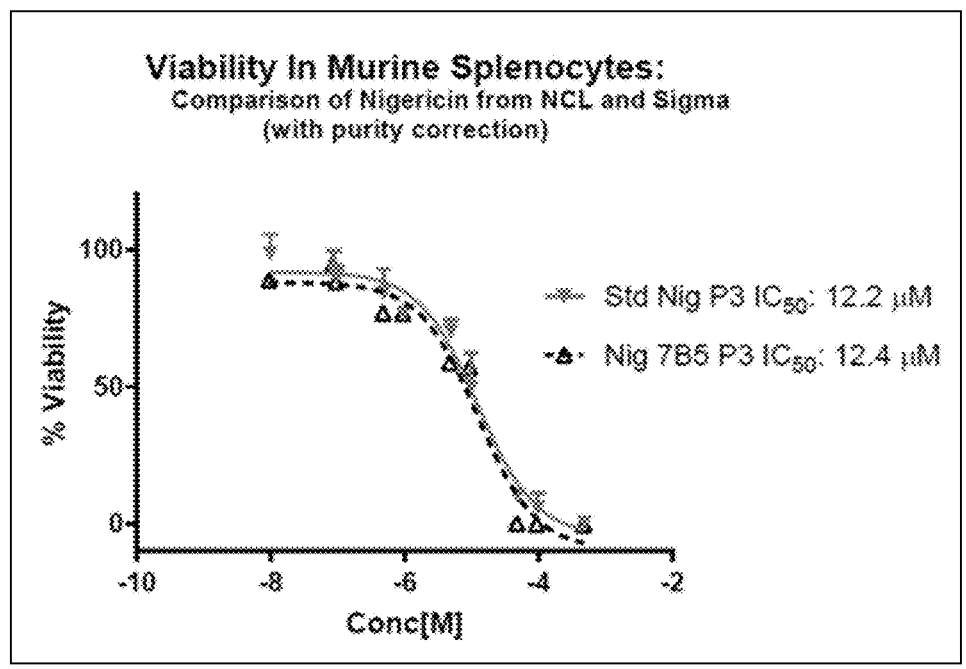
FIG. 3 depicts a comparison of the in-vitro toxicity of nigericin isolated from *Streptomyces* sp. MCC-0151 and commercially available Nigericin on murine splenocytes. '▲' represents nigericin from *Streptomyces* sp. MCC 0151 and '▼' represents standard Nigericin.

FIG. 3 shows the comparative toxicity of Nigericin from *Streptomyces* sp. MCCO151 and Sigma standard nigericin. Nigericin produced from *Streptomyces* sp. MCCO151 exhibited no statistically significant difference with respect to its toxicity against murine splenocytes when compared to commercially available nigericin (Sigma).

Example 7

Plasma Pharmacokinetics of Nigericin to Male Sprague Dawley Rats

Intravenous: Following a single intravenous administration of nigericin to male Sprague Dawley rats at 2 mg/kg dose, nigericin has shown moderate plasma clearance (15.10 mL/min/kg, the normal liver blood flow in rat=55 mL/min/kg) with a mean elimination half-life of 3.53 hr. The Vss was 2.3-fold higher than the normal volume of total body water (0.7 L/kg).

Oral: Following a single oral administration of nigericin to male Sprague Dawley rats at 10 mg/kg dose, plasma concentrations were quantifiable up to 24 hr with $T_{max}$ at 0.63 hr. Oral solution bioavailability was 2%.

Intraperitoneal: Following a single intraperitoneal administration of nigericin to male Sprague Dawley rats at 2 mg/kg dose, plasma concentrations were quantifiable up to 24 hr with $T_{max}$ at 0.25 hr.

Figure 4:
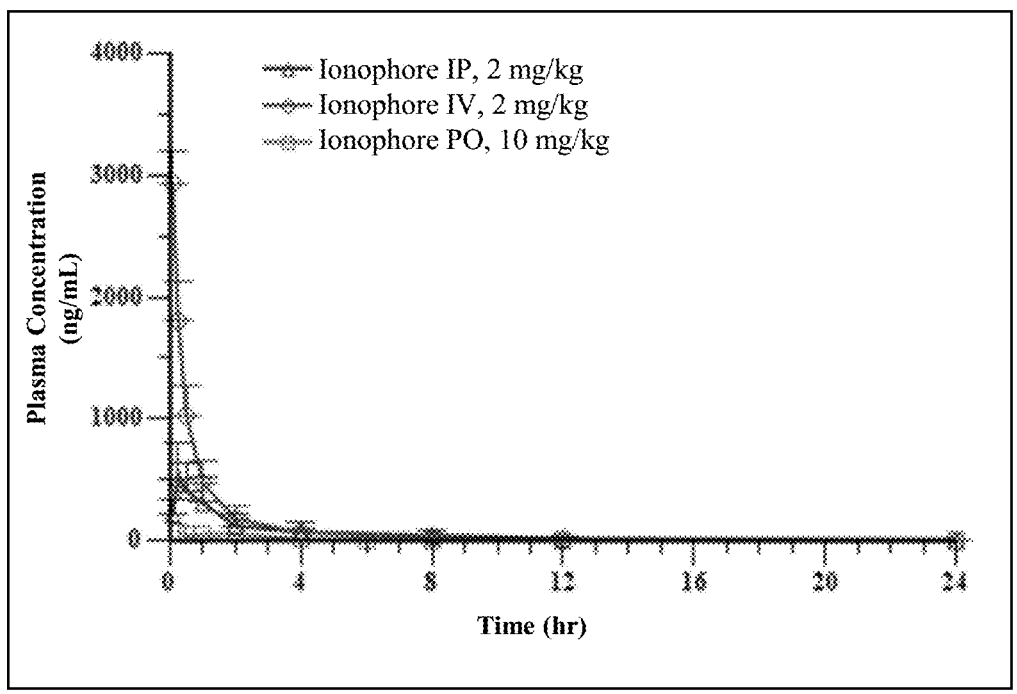
FIG. 4 depicts the Mean plasma concentration-time profiles of nigericin from *Streptomyces* sp. MCC 0151 following a single intravenous (IV, Dose: 2 mg/kg), intraperitoneal (IP, Dose: 2 mg/kg) and oral (PO, Dose: 10 mg/kg) administration in male Sprague Dawley rats.

FIG. 4 depicts the Mean plasma concentration-time profiles of nigericin from *Streptomyces* sp. MCCO151 following a single intravenous (IV, Dose: 2 mg/kg), intraperitoneal (IP, Dose: 2 mg/kg) and oral (PO, Dose: 10 mg/kg) administration in male Sprague Dawley rats.

Plasma Pharmacokinetics study of Nigericin was carried out using three different routes of administration i.e. Intravenous (IV), Oral (O) and Intraperitoneal (IP). Based on above study, the intraperitoneal route of administration was selected to study the toxicokinetic profiling of Nigericin.

Example 8

Toxico-Kinetic Study of Nigericin in Sprague-Dawley Rats Following Intraperitoneal Administration A 14-day repeat-intraperitoneal administration protocol was used for carrying out toxicokinetic studies with nigericin. Male and female animals were divided into three groups each based on the dose of nigericin administered (0.5, 1.5 and 5 mg/kg/day). Each group received the administration of the compound at the same dose every day for 14 days. The toxicokinetic parameters were quantified following the first (i.e., day-1) and last (i.e., day-14) administration of nigericin, and the findings are tabulated in Table-3. Following administration on day-1, nigericin was quantifiable in the plasma of the animals for up to 24 h, in all three dose-categories, in both genders. After the administration of the second dose on day-14, plasma concentrations were quantifiable up to 8 h for 0.5 mg/kg/day dose category and up to 24 h for 1.5 mg/kg/day dose category, in both genders. However, for the 5 mg/kg/day dose category, plasma concentrations of nigericin were quantifiable up to 24 h in male rats only, since mortality was observed in case of female rats in this category before Day 14.

Mean $T_{max}$ on Day 1 and Day 14 across the doses ranged from 0.08-0.42 h. However, dose-related increase in the plasma exposure ($AUC_{last}$) with the increase in dose was observed on both the days i.e. Day 1 and Day 14 respectively.

Mortality was observed in female group of animals at 5 mg/kg/day before Day 14. Plasma concentrations on Day 14 were quantifiable till 8 hr at 0.5 mg/kg/day and till 24 hr at 1.5 mg/kg/day dose group across the gender and 5 mg/kg/day dose group in male rats. Mean $T_{max}$ on Day 1 and Day 14 across the doses ranged 0.08-0.42 hr. However, dose-related increase in plasma exposure ($AUC_{last}$) with increase in doses was observed on both the days i.e. Day 1 and Day 14.

Dose exposure ratio, with an increase in dose from 0.5 to 1.5 mg/kg/day and 1.5 to 5 mg/kg/day was 1.91 and 3.93 respectively on Day 1; and 3.89 and 4.26 on Day 14 in males Sprague Dawley rats. Dose exposure ratio females Sprague Dawley rats was 5.91 and 2.33 on Day 1 and 2.89 (0.5 to 1.5 mg/kg/day) on Day 14. No trend of accumulation was observed across the doses and in both the genders following repeated intraperitoneal dose administration. The accumulation ratio ($AUC_{last}$) on Day 14 was found to be 0.44 (0.5 mg/kg/day), 0.90 (1.5 mg/kg/day) and 0.98 (5 mg/kg/day) in male Sprague Dawley rats, while in female rats the ratio was 1.04 (0.5 mg/kg/day) and 0.51 (1.5 mg/kg/day). No gender-specific difference was observed across the doses on Day 1 and Day 14 except at 0.5 mg/kg dose on Day 1 (male/female exposure ratio 2.11). The male/female exposure ratio (AU-$C_{last}$) was found to be 2.11 (0.5 mg/kg/day), 0.68 (1.5 mg/kg/day) and 1.15 (5 mg/kg/day) on Day 1 and 0.90 (0.5 mg/kg/day) and 1.21 (1.5 mg/kg/day) on Day 14. No significant gender-specific differences were observed across the doses from Day 1 and Day 14, except in case of 0.5 mg/kg/day dose category on Day 1, where the male/female exposure ratio was 2.11. Male/female exposure ratio (AU-$C_{last}$) values for all the groups are tabulated in Table-3.

Figure 5:
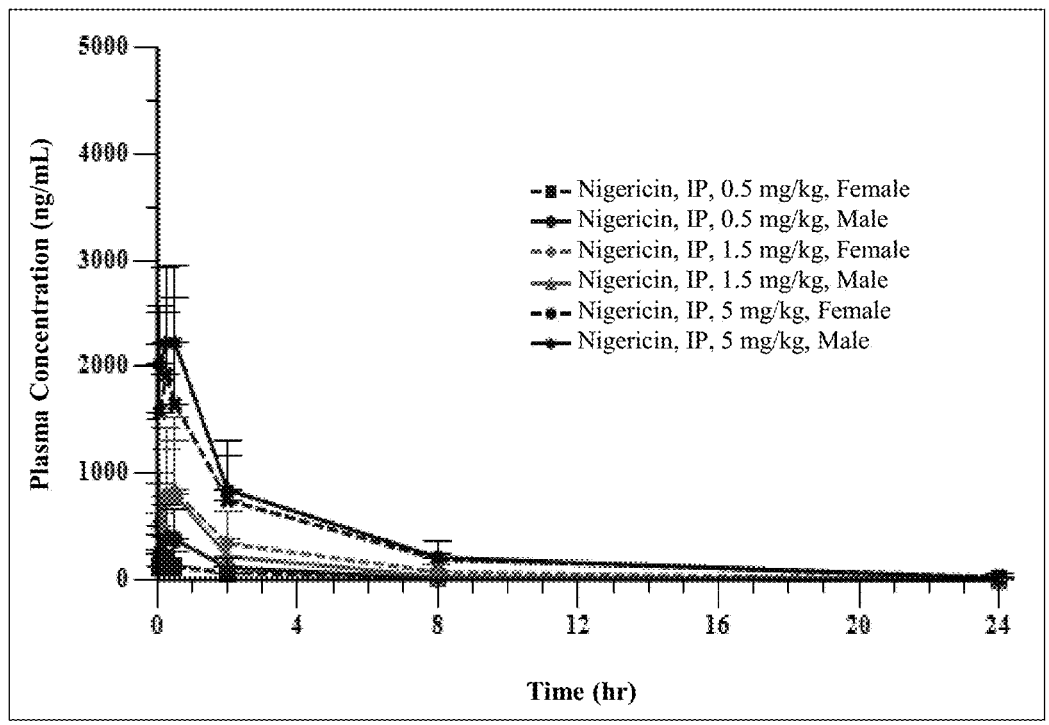
FIG. 5 depicts the plasma concentration-time profiles in male and female Sprague-Dawley rats following 14 day repeated intraperitoneal administration of nigericin from *Streptomyces* sp. MCC 0151 on Day 1 (Dose: 0.5, 1.5 and 5 mg/kg/day).

FIG. 5 depicts the plasma concentration-time profiles in male and female Sprague-Dawley rats following 14 day repeated intraperitoneal administration of nigericin from Streptomyces sp. MCC0151 on Day 1 (Dose: 0.5, 1.5 and 5 mg/kg/day).

TABLE 3

Mean toxicokinetics parameters (n = 3) in male and female Sprague-Dawley rats[a]

| Gender | Day | Dose (mg/kg/day) | $T_{max}$ (h) | $C_{max}$ (ng/mL) | $AUC_{last}$ (h*ng/mL) |
|---|---|---|---|---|---|
| Male | 1 | 0.5 | 0.25 | 402.52 | 1114.72 |
| | | 1.5 | 0.33 | 829.88 | 2126.23 |
| | | 5.0 | 0.33 | 2392.98 | 8347.82 |
| | 14 | 0.5 | 0.28 | 199.50 | 494.18 |
| | | 1.5 | 0.08 | 814.87 | 1921.46 |
| | | 5.0 | 0.33 | 3058.75 | 8187.87 |
| Female | 1 | 0.5 | 0.33 | 188.42 | 527.43 |
| | | 1.5 | 0.42 | 840.17 | 3116.73 |
| | | 5.0 | 0.33 | 2437.83 | 7262.87 |
| | 14 | 0.5 | 0.33 | 222.17 | 549.87 |
| | | 1.5 | 0.19 | 710.63 | 1589.38 |
| | | 5.0 | NC | NC | NC |

[a]14 days repeated intraperitoneal administration of Nigericin on Day 1 and Day 14 (Dose: 0.5, 1.5 and 5 mg/kg/day).
NC: not calculated as samples were missing due to animal mortality Nigericin administered to Sprague-Dawley rats, once a day for 14 consecutive days by intraperitoneal route at 0.5, 1.5 and 5 mg/kg/day, did not result in abnormal clinical signs at 0.5 mg/kg/day and mortalities up to 1.5 mg/kg/day. There was no test item related effect on ophthalmoscopy, coagulation, urinalysis and reticulocytes count up to highest surviving dose 1.5 mg/kg/day. The 5 mg/kg/day was lethal in females.

Hence in the present study conditions, it can be concluded that nigericin at a dose <1.5 mg/kg will not cause any clinical adversity. However the dose above 5 mg/kg can be lethal.

Example 9

Antibacterial Activity of Nigericin Synthesized by Streptomyces MCC-0151

Figure 1A:
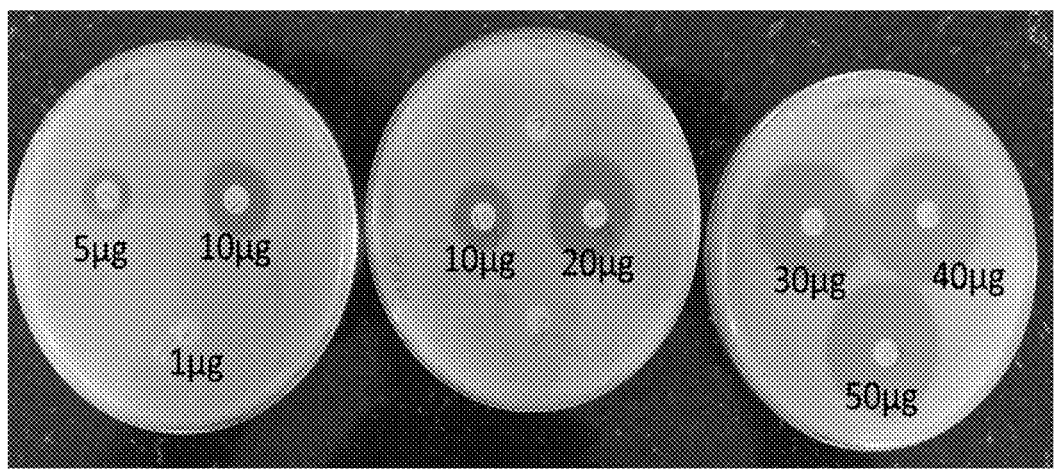
FIG. 1A depicts the inhibition of *S. aureus* growth at varying concentrations of nigericin from *Streptomyces* sp. MCC-0151.
Figure 1B:
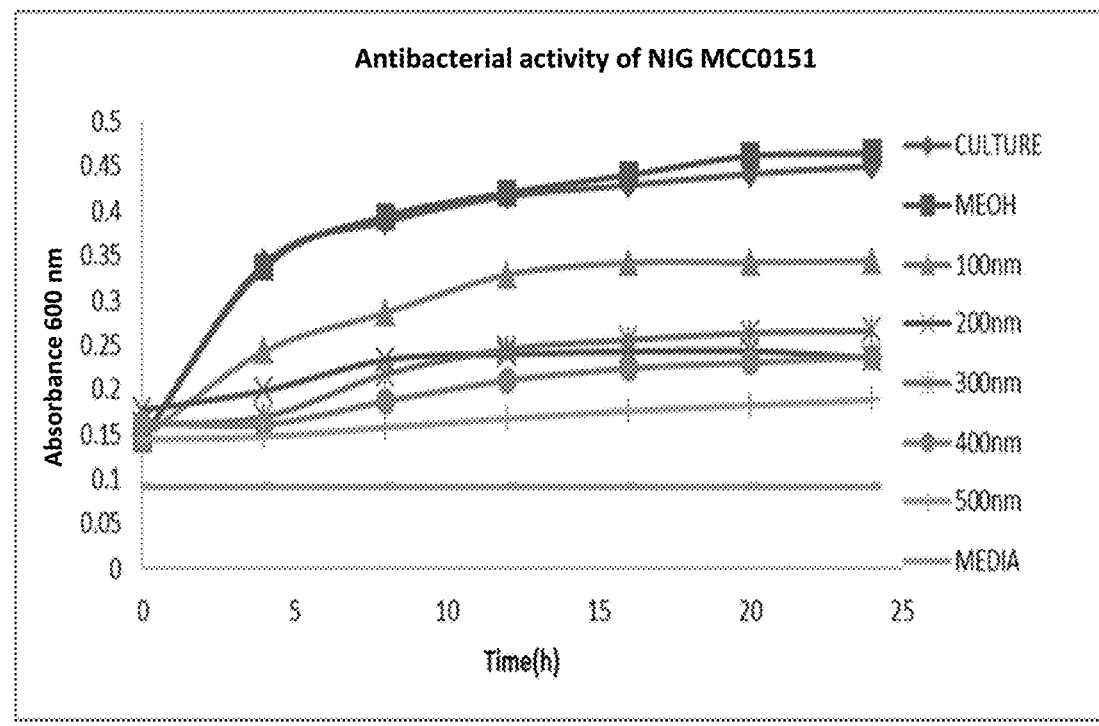
FIG. 1B depicts the antibacterial activity of nigericin from *Streptomyces* sp. MCC 0151 against *S. aureus*.

Nigericin synthesized by Streptomyces sp MCCO151 using the process of the present disclosure was found to be active against gram-positive microorganisms Staphylococcus aureus (ATCC 29737), Staphylococcus epidermidis (ATCC 12228), Micrococcus luteus (ATCC 11880), Bacillus cereus (ATCC 11778) and Listeria monocytogenes (ATCC 19111) with minimum inhibitory concentration (MIC) ranging from 250 to 500 nM. FIG. 1A depicts the inhibition of S. aureus growth at varying concentrations of nigericin from Streptomyces sp. MCC-0151. FIG. 1B depicts the antibacterial activity of nigericin from Streptomyces sp. MCC0151 against S. aureus.

Figure 1C:
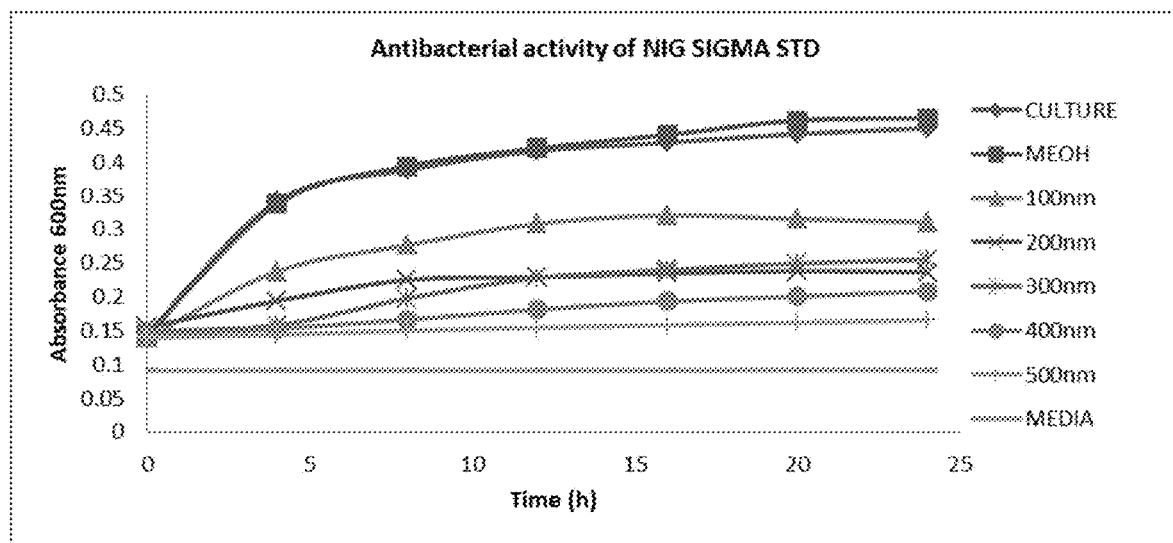
FIG. 1C depicts the antibacterial activity of sigma standard nigericin against *S. aureus*.

FIG. 1C depicts the antibacterial activity of sigma standard nigericin against S. aureus.

From this experiment, it can be concluded that nigericin synthesized by Streptomyces MCC-0151 showed excellent anti-bacterial potency. The nigericin nigericin has MIC of 0.21 g/mL against Staphylococcus aureus and MIC Conc. of 287.7 nM.

Example 10

Antimalarial Activity of Nigericin Synthesized by Streptomyces MCC-0151

Asexual stage of P. falciparum strain 3D7 (received as a gift from collaborator team) was maintained under standard conditions at 2% hematocrit with 0+ human erythrocytes (Blood obtained from Poona Serological Trust Blood Bank, Pune) in RPMI1640 containing 15 mM HEPES, 50 mg/L Gentamicin sulfate 10 mg/L hypoxanthine, 2 g/L sodium bicarbonate (Sigma-Aldrich) and 2.5 g/L AlbuMAX II (Thermo Fisher Scientific). Parasites were synchronized using 5% sorbitol (Sigma-Aldrich) for the enrichment of ring-stage parasite. In brief, P. falciparum cultures were collected by centrifugation at 1,000 g for 5 min at 25° C. and the parasitized RBC pellet was resuspended 5% sorbitol, followed by incubation at 37° C. for 10 min. Following incubation, the cells were pelleted and washed with complete medium, prior to placing the parasites back into culture flasks at 2% hematocrit and 2% parasitemia.

Figure 2:
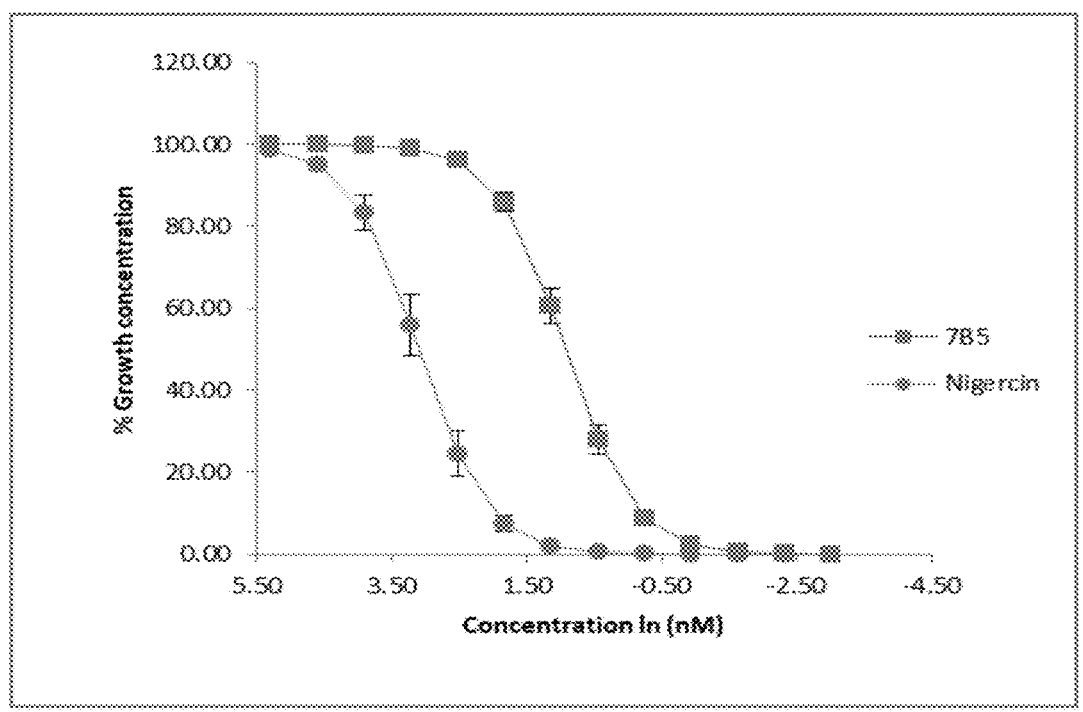
FIG. 2 depicts the $EC_{50}$ values for inhibition of blood-stage malaria parasite growth. '■' represents nigericin from *Streptomyces* sp. MCC 0151 and '●' represents standard Nigericin. The number of replicates n=3 for all samples.

Assays were typically set up in 96-well plate format and 2% of parasitized culture was used per well. The stock solution of the nigericin was prepared in DMSO, and so 0.5% DMSO (equivalent to the DMSO present in the nigericin-treated samples) treatment was used as a control. Assay incubation was carried out for 60 h under optimal conditions for P. falciparum growth after which the culture samples were lysed with 0.01% triton X and stained with SybrGreen I nucleic acid stain to estimate the relative growth of parasites in each sample. Results are reported as % of growth inhibition and active molecule tested further to determine the IC50 values of compound. FIG. 2 depicts the $EC_{50}$ values for inhibition of blood-stage malaria parasite growth. '■' represents nigericin from Streptomyces sp. MCC0151 and '●' represents standard Nigericin. The number of replicates n=3 for all samples. The antimalarial $EC_{50}$ value for nigericin isolated from Streptomyces sp. MCC0151 was 2.4 nM. It was determined that nigericin has $IC_{50}$ ~0.986 nM against P. falciparum.

ADVANTAGES

1. Nigericin from Streptomyces hygroscopicus is obtained as a contaminant during commercial production of geldanamycin as known in the art, whereas the present disclosure provides a process for synthesis of nigericin from a Streptomyces sp. MCC 0151, wherein nigericin is the major metabolite with high yield.

2. The process for synthesis of nigericin from Streptomyces sp. MCC 0151 of the present disclosure yields 33% Nigericin with high purity.

3. The process for synthesis of nigericin from a Streptomyces sp. MCC 0151 of the present disclosure can be used for the production of nigericin at an industrial scale at a significantly lower investment.

We claim:

1. A process for synthesis of nigericin from *Streptomyces* sp. MCC 0151, the process comprising:
   (i) providing a pure colony of *Streptomyces* sp. MCC 0151;
   (ii) preparing an inoculum by incubating the pure colony of *Streptomyces* sp. MCC 0151 in liquid cultivation medium (LCM);
   (iii) providing a metabolite production medium;
   (iv) aseptically inoculating the inoculum from (ii) to the metabolite production medium and culturing the inoculum therein;
   (v) mixing the metabolite production medium containing the *Streptomyces* sp. MCC 0151 and ethyl acetate in a ratio of 1:1 to obtain a mixture;
   (vi) centrifuging the mixture obtained in (v) to obtain a supernatant and an ethyl acetate extract comprising nigericin;
   (vii) evaporating the ethyl acetate extract obtained in (vi) to obtain a dried crude extract; and
   (viii) purifying the dried crude extract obtained in (vii) by column chromatography to obtain a purified nigericin, wherein nigericin is produced having a high yield with concentration up to 500 mg/L.

2. The process of claim 1, wherein the inoculation in step (iv) is effected by providing the inoculum from step (ii) in a concentration from 5% to 10% of the total volume of the metabolite production medium.

3. The process of claim 1, wherein the culturing is carried out at a temperature range of 28° C. to 32° C. for 5 days to 8 days.

4. The process of claim 1, wherein the column chromatography comprises a silica gel mesh as a stationary phase and a gradient comprising dichloromethane and methanol as a mobile phase.

5. The process of claim 1, wherein the metabolite production medium comprises a carbon source, yeast extract as a nitrogen source, $K_2HPO_4$, and $MgSO_4 \cdot 7H_2O$ at pH of 7.0±0.3.

6. The process of claim 5, wherein the carbon source is starch.

7. The process of claim 1, wherein the nigericin produced has a yield of 33% by weight of dried crude extract.

8. The process of claim 1, wherein the nigericin produced has an anti-bacterial and anti-malarial property.

9. The process of claim 1, wherein the LCM comprises soya meal, mannitol, and glucose at pH of 7.0±0.3.

\* \* \* \* \*